(12) United States Patent
Hayashizaki et al.

(10) Patent No.: US 7,531,076 B2
(45) Date of Patent: May 12, 2009

(54) CAPILLARY CASSETTE AND METHOD OF MANUFACTURING THE SAME

(75) Inventors: Yoshihide Hayashizaki, Ibaraki-ken (JP); Rintaro Yamamoto, Kyoto (JP)

(73) Assignees: The Institute of Physical and Chemical Research, Wako-shi (JP); Shimadzu Corporation, Kyoto (JP); Japan Science and Technology Agency, Kawaguchi-shi (JP)

( * ) Notice: Subject to any disclaimer, the term of this patent is extended or adjusted under 35 U.S.C. 154(b) by 693 days.

(21) Appl. No.: 11/326,368

(22) Filed: Jan. 6, 2006

(65) Prior Publication Data
US 2006/0113191 A1    Jun. 1, 2006

Related U.S. Application Data

(62) Division of application No. 10/401,862, filed on Mar. 31, 2003, now Pat. No. 7,014,745, which is a division of application No. 09/402,890, filed as application No. PCT/JP99/00653 on Feb. 15, 1999, now Pat. No. 6,560,859.

(30) Foreign Application Priority Data

| Feb. 16, 1998 | (JP) | ................................. 10-51489 |
| Feb. 16, 1998 | (JP) | ................................. 10-51490 |
| Feb. 16, 1998 | (JP) | ................................. 10-51491 |
| Feb. 16, 1998 | (JP) | ................................. 10-51492 |

(51) Int. Cl.
*G01N 27/453* (2006.01)

(52) U.S. Cl. ..................................... 204/605; 204/601

(58) Field of Classification Search ......... 204/601–605, 204/451–455
See application file for complete search history.

(56) References Cited

U.S. PATENT DOCUMENTS

| 5,332,481 A | 7/1994 | Guttman |
| 5,366,608 A | 11/1994 | Kambara |

(Continued)

FOREIGN PATENT DOCUMENTS

EP    0 395 218    10/1990

(Continued)

OTHER PUBLICATIONS

Supplementary Partial European Search Report dated Feb. 25, 2003, for appln. No. EP99903923.

(Continued)

*Primary Examiner*—Alex Noguerola
(74) *Attorney, Agent, or Firm*—Westerman, Hattori, Daniels & Adrian, LLP.

(57) ABSTRACT

Capillary columns (102) pass through and are inserted in a rubber plate (14), held and fixed by elastic force of rubber, and two-dimensionally arranged on a sample injection side. it fixes the capillary columns (102) arranged on a plane in close contact by holding the same with a holder plate (6a) from below and with a rubber plate (16) from above on a detection side. In order to press the capillary columns (102) against the holder plate 6a and fix the same with the rubber plate (16), a holder plate (6b) fixing the rubber plate (16) to the holder plate (6a) on both sides of the arrangement of the capillary columns (102) is provided.

4 Claims, 13 Drawing Sheets

U.S. PATENT DOCUMENTS

| | | |
|---|---|---|
| 5,417,925 A | 5/1995 | Goodale et al. |
| 5,458,761 A | 10/1995 | Kamahori et al. |
| 5,498,324 A | 3/1996 | Yeung et al. |
| 5,560,811 A | 10/1996 | Briggs et al. |
| 5,567,294 A | 10/1996 | Dovichi et al. |
| 5,605,666 A | 2/1997 | Goodale et al. |
| 5,635,050 A | 6/1997 | Pentoney, Jr. et al. |
| 5,695,626 A | 12/1997 | Yeung et al. |
| 5,741,411 A | 4/1998 | Yeung et al. |
| 5,744,100 A | 4/1998 | Krstanovic |
| 5,858,194 A | 1/1999 | Bell |
| 5,885,430 A | 3/1999 | Kernan et al. |
| 6,027,627 A | 2/2000 | Li et al. |
| 6,054,032 A | 4/2000 | Haddod et al. |
| 6,103,083 A | 8/2000 | Merenkora et al. |
| 6,120,667 A | 9/2000 | Hayashizaki et al. |
| 6,231,739 B1 | 5/2001 | Nordman et al. |
| 6,428,670 B1 | 8/2002 | Hayashizaki et al. |
| 6,461,492 B1 | 10/2002 | Hayashizaki et al. |

FOREIGN PATENT DOCUMENTS

| | | |
|---|---|---|
| EP | 0854362 A2 | 7/1998 |
| JP | 5-72177 | 3/1993 |
| JP | 6-138037 | 5/1994 |
| JP | 8-193976 | 7/1996 |
| WO | WO 93/17325 | 9/1993 |
| WO | WO 98 14773 A | 4/1998 |
| WO | WO 99/00664 | 1/1999 |

OTHER PUBLICATIONS

Lux, J.A. et al., "Production of Windows in Fused Silica Capillaries for In-Column Detection of UV-Absorption or Fluorescence in Capillary Electrophoresis or HPLC", Journal of High Resolution Chromatography, May 1, 1990, vol. 13, No. 5, pp. 373-374, Wiley VCH.

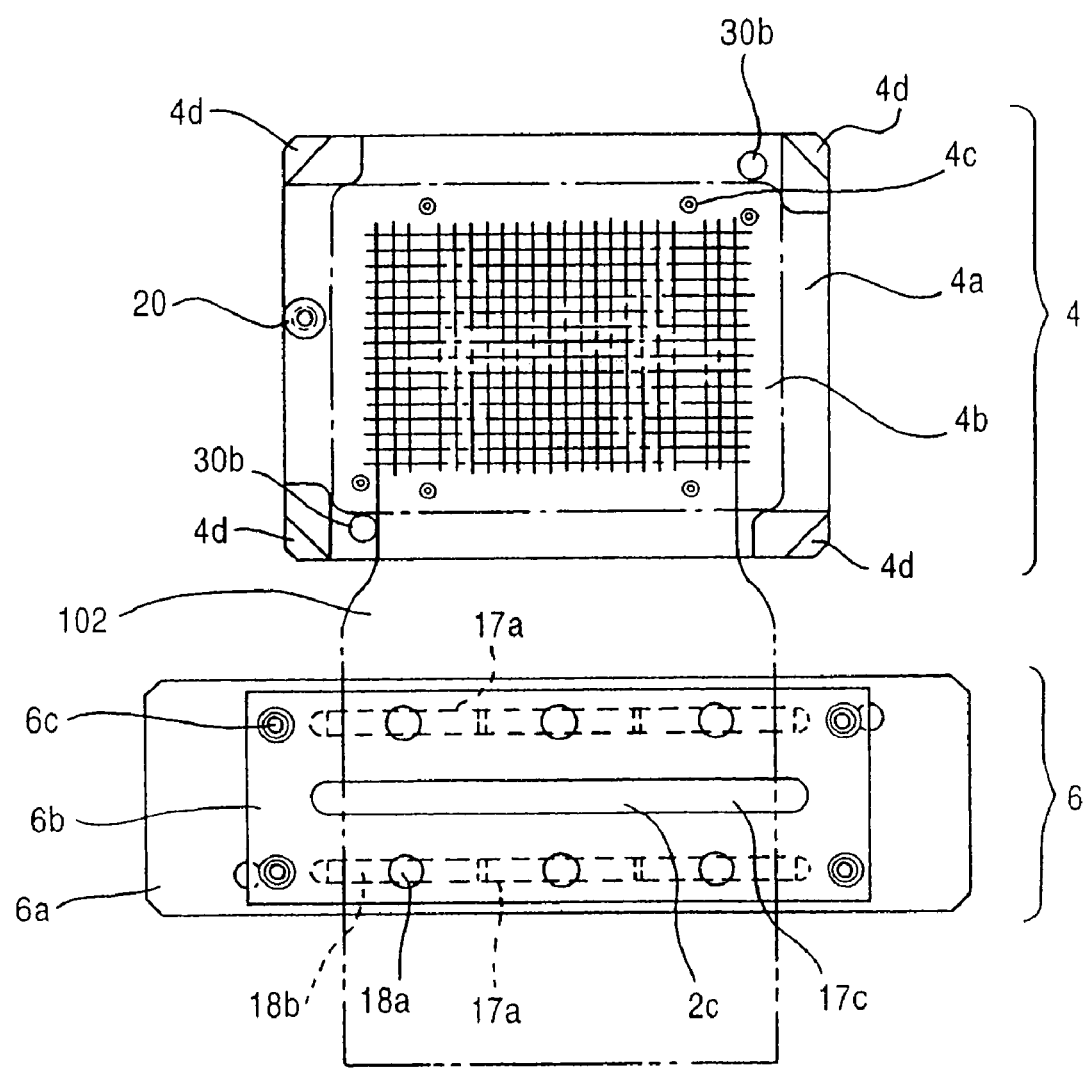

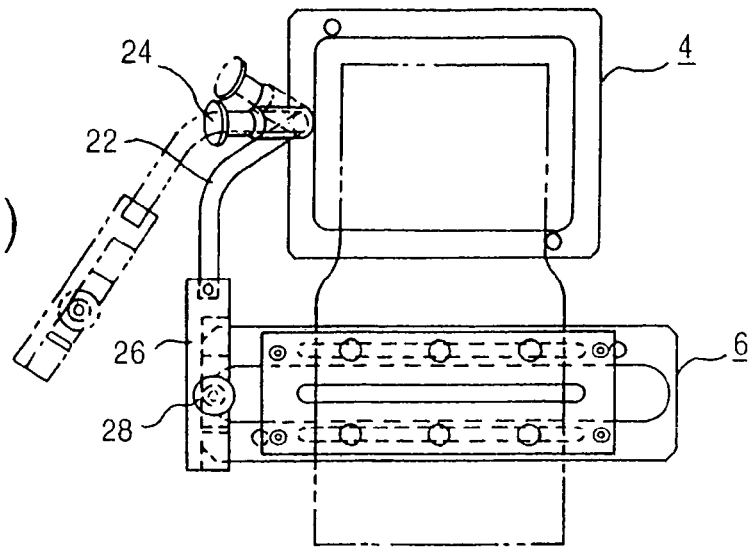
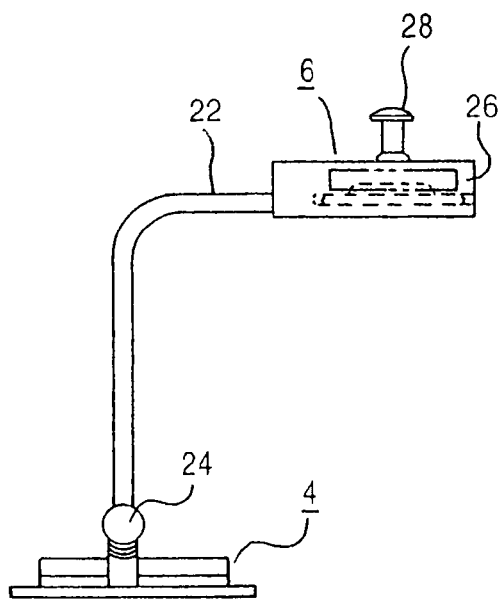
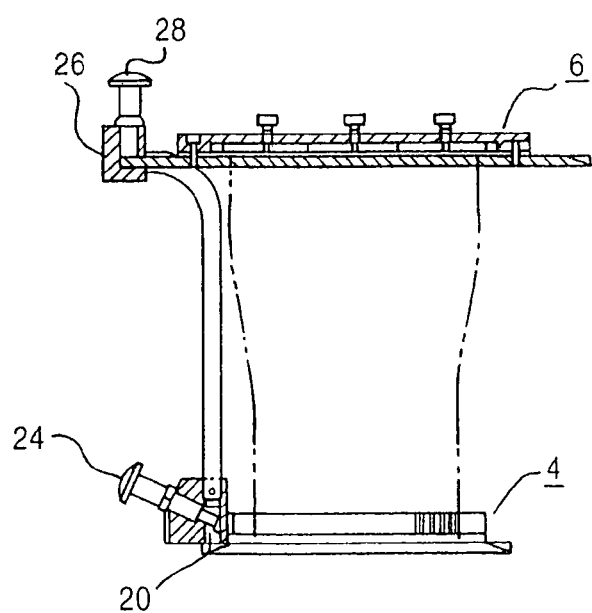
Fig.5(C)
Fig.5(B)
Fig.5(A)

CAPILLARY CASSETTE AND METHOD OF MANUFACTURING THE SAME

This application is a divisional of U.S. application Ser. No. 10/401,862, filed Mar. 31, 2003; now U.S. Pat. No. 7,014,745; which is a divisional of U.S. application Ser. No. 09/402,890, filed Oct. 14, 1999; now U.S. Pat. No. 6,560,859; which is a 35 U.S.C. 371 application of international application no. PCT/JP99/00653 filed Feb. 15, 1999.

TECHNICAL FIELD

The present invention relates to, in a multi-capillary electrophoretic apparatus comprising such a multi-capillary array migration part that a plurality of capillary columns are arranged so that samples are injected into the respective capillary columns and simultaneously electrophoresed in all capillary columns and an optical measuring part irradiating capillaries with light in the multi-capillary array migration part and measuring absorbance by the samples in the irradiated parts and fluorescence from the samples, a capillary cassette forming the multi-capillary array migration part.

Such a multi-capillary electrophoretic apparatus is used for separating/analyzing nucleic acid, protein, peptide, sugar and the like, and particularly plays an important role for analysis of the base sequence of DA. The multi-capillary electrophoretic apparatus for sequence determination of DNA employs Sanger's reaction, electrophoreses a DNA fragment (fragment) sample labeling a primer or a terminator with a fluorescent material and detects fluorescence from the DNA fragment sample during migration for deciding the base sequence.

BACKGROUND TECHNIQUE

For sequence determination of DNA having long base sequence such as a human genome, a DNA sequencer having high sensitivity, a high speed and large throughput is necessary. As one method thereof, a multi-capillary DNA sequencer arranging capillary columns charged with gels in plural is proposed in place of that employing flat plate type slab gels. In the capillary column, a sample is not only easy to handle or inject but also can be migrated at a high speed and detected in high sensitivity as compared with the slab gel. Namely, such problems result from influence by Joulean heat that a band spreads and a temperature gradient takes place applying a high voltage in the slab gel, while such problems are less in the capillary column and spreading of a band is small to allow high sensitivity detection even if making high-speed migration while applying a high voltage.

When making electrophoresis employing a plurality of capillary columns, it is desirable that attachment/detachment of the capillary columns to/from an electrophoretic apparatus body is easy, and it is desirable to cassette the same with a holder for that. In consideration of the recent environmental problem, it is also preferable that the capillary columns can be readily separated from the holder when discarded after use.

Furthermore, since a step by pressurization or decompression is requisite for charging gels into the capillary columns, airtightness is necessary for fixation of the capillary columns to the holder at least on sample injection sides in order to simultaneously charge the gels into all capillary columns contained in the cassette.

Accordingly, a first objective of the present invention is to provide a capillary cassette which can readily separate capillary columns from a holder and has sufficient airtightness between the capillary columns and the holder on sample injection sides.

The capillary columns are so thin that the same are difficult to manually work and are easily breakable. When fixing the capillary columns to the holder, it is a difficult operation requiring skill to bundle the same in plural, and in addition, it requires a long time.

Accordingly, a second objective of the present invention is to make it possible to simply and quickly perform preparation of a capillary cassette.

The capillary columns are protected with various coats, in order to increase mechanical strength. For coats, polyimide, silicone resin, polytetrafluoroethylene, acrylic resin and the like are used. When using the same as coats for capillary columns of electrophoresis however, optical characteristics of the coats such as light absorption and fluorescence hinder detection since optical means for absorbance measurement and fluorescence measurement are employed for detection of samples migrating in the capillary columns. Therefore, when the coats are made of materials hindering optical detection, the coats of detection parts are burned by flames and removed with burning means such as a lighter or a gas burner.

A multi-capillary electrophoretic apparatus using a plurality of capillary columns and simultaneously detecting a plurality of samples aligns, arranges and fixes such capillary columns that coats of detection parts are removed, thereby forming detection windows when the coats are made of materials hindering optical detection.

While a number of capillary columns are arranged in the multi-capillary electrophoretic apparatus, it follows that when performing coat removal of the detection parts on every one of the capillary columns, a long time is required for the operation.

Furthermore, the coating materials include such a one that a part located in a flame is completely burned and removed in the process of removing the coating material by burning by the flame while the same is melted but does not come to be removed in a portion separate from the flame and convex parts resulting from solidification of the melted coat are formed on both sides of the part from which the coat is removed. If such convex portions are formed, adjacent capillary columns do not adhere to each other or come to different levels due to the convex portions and detection windows are not planarly aligned when arranging the capillary columns, aligning positions of the parts from which the coats are removed and forming the detection windows. Consequently, the focus of an optical system may so deviate in detection that it cannot perform proper detection.

Accordingly, a third objective of the present invention is, when a coat for a capillary column is made of a material hindering optical detection, to provide such a capillary cassette that a detection window of a capillary column employed for a multi-capillary electrophoretic apparatus is planarly formed to be suitable for optical measurement and a method of manufacturing a capillary cassette having a feature in a detection window forming step thereof.

An initial capillary electrophoretic apparatus is that employing a single-capillary column. In this case, it dips an end of the capillary column into a gel solution in a vessel, closes the vessel and pressurizes the vessel thereby pushing the gel into the capillary column and charging the same as a method of charging the gel into the capillary column. As another method, an operation of dipping an end of the capillary column into the gel solution, decompressing another end of the capillary column and sucking the gel into the capillary column, thereby charging the same, is also performed.

In multi-capillary electrophoresis, it is necessary to align capillary column end surfaces on sample injection sides in sample injection while it is necessary to align and handle capillary coat removing parts on detection sides when performing detection for handling a plurality of capillary columns, and hence it is desirable to provide such a capillary cassette that arrangement is fixed by a holder so that both the sample injection sides and the detection sides are in prescribed arrangement relation.

Furthermore, it is extremely troublesome to charge a gel into every one of the capillary columns in the state of the capillary cassette, and, in actuality, impossible in practice. Therefore, awaited is means for making it possible to simply perform gel charging into all capillary columns included therein in units of the capillary cassette.

Accordingly, a fourth objective of the present invention is to provide an apparatus to make it possible to simply charge gels into all capillary columns included in such a capillary cassette.

DISCLOSURE OF THE INVENTION

In order to attain the first objective, the present invention is such that, in a capillary cassette two-dimensionally arranging and fixing a plurality of capillary columns used in a multi-capillary electrophoretic apparatus on sample injection sides by a holder while arranging the same in a line on a plane on detection sides (sides opposite to the sample injection sides), the holder comprises a rubber plate so that end portions of the plurality of capillary columns pass through the rubber plate one by one to be fixed by elastic force of the rubber plate.

By inserting the capillary columns into the rubber plate and fixing the same with the holder on the sample injection sides, airtightness between the rubber plate and the capillary columns can be maintained and it is possible to serve a sealing function with respect to pressurization or suction in gel charging into capillaries. The capillary columns are not fixed by an adhesive or the like, whereby the capillary columns can be readily extracted from the holder in disposal of the capillary columns or the like.

In the present invention, it is preferable to comprise another holder pressing and holding the capillary columns from at least single surface sides of the plurality of capillary columns arranged in a line on the plane through the rubber plate on the detection sides of the capillary columns. By thus making fixation on the detection sides by pushing the capillary columns through the rubber plate, it is easy to detach the capillary columns from the holder on the detection sides, and an operation of separating the capillary columns and the holder in disposal after use or exchanging defective capillary columns becomes easy.

Furthermore, the holder on the detection sides preferably comprises clamping means fixing the capillary columns on both side portions while pressing and fixing the same on at least two portions of an intermediate part as means fixing the plurality of capillary columns arranged in a line on the plane through the rubber plate. By making it possible to press the capillary columns also in at least two portions of the intermediate part, it becomes easy to maintain arrangement on the plane.

A capillary cassette preparation method according to the present invention to attain the second objective is a method of passing through a supporter of a prescribed fixing position of capillary column fixing means having the supporter consisting of a rubber plate with a needle having an inner diameter larger than a capillary column from its vertical direction, guiding the capillary column into the needle and making the same pass through the supporter, thereafter extracting only the needle thereby holding and fixing the capillary column by the supporter and repeating this operation while changing the fixing position on the supporter thereby successively two-dimensionally arranging and fixing a plurality of capillary columns.

The capillary column guided in the needle to pass through the supporter of the rubber plate on a sample injection side holder (capillary column fixing means) is held and fixed by elastic force of rubber after only the needle is extracted from the supporter.

A capillary cassette preparation apparatus according to the present invention for executing this capillary cassette preparation method comprises arrangement position decision means holding capillary column fixing means having a supporter consisting of a rubber plate for moving and fixing the same in an in-plane direction of the supporter, a needle passing through the supporter comprised in the capillary column fixing means from a vertical direction of its plane and guiding a capillary column to the fixing position, a first capillary column holder holding the capillary column and inserting the same into the needle, a guide guiding the forward end of the capillary column held by the first capillary column into the needle, slide guide means moving the needle, the guide and the first capillary column holder in a rectilinear direction perpendicular to the plane of the supporter, a second capillary column holder holding the forward end portion of the capillary column made to project from the forward end of the needle in such a state that the needle passes through the supporter of the capillary column fixing means, cut means cutting the capillary column in a prescribed length, and a roller unit successively feeding the capillary column in an insert direction.

The fixing position of the capillary column is decided by mounting the capillary column fixing means on the arrangement position decision means and moving the arrangement position decision means upward, downward, leftward and rightward. It linearly moves the needle in the capillary column fixing means direction along the slide guide means and makes the same pass through the supporter on the fixing position. The forward end of the capillary column wound on a capillary drum is guided into the needle by the guide following the needle along the slide guide means and the first capillary column holder, and projects from the forward end of the needle. It holds the forward end portion of the capillary column by the second capillary column holder comprised on a needle projection side of the arrangement position decision means, and extracts only the needle from the supporter of the capillary column fixing means. The capillary column forward end portion remains in the supporter, elastic force of rubber which is the supporter acts in a direction closing a hole opened by the needle, and the capillary column is fixed to the capillary column fixing means. It cuts the fixed capillary column in the prescribed length by the cut means. The arrangement position decision means moves and brings a next fixing position onto a moving straight line of the needle, the guide and the capillary column holder. The capillary column wound on the drum is timely fed by the roller unit having a motor for motive power.

According to this capillary cassette preparation apparatus, capillary columns of a predetermined length are aligned in determined order by operating a lever in accordance with a prescribed procedure so that a capillary cassette can be prepared, whereby the efficiency of a preparation operation for the capillary cassette remarkably rises. Furthermore, it can simply make transition to automatization by mounting a driving source, whereby simple preparation of a capillary cassette with less failure is enabled.

In order to also form detection windows simultaneously with capillary cassette preparation, it is preferable to further comprise detection window preparation means removing capillary column coats of prescribed positions from the forward ends of the capillary columns and preparing the detection windows and arrangement means arranging terminating end sides of the cut capillary columns in a line in determined order in the capillary cassette preparation apparatus.

After the capillary columns are guided in the needle and pass through the capillary column fixing means, a voltage is applied to the detection window preparation means to prepare the detection windows on prescribed positions from the forward ends of the capillary columns. Thereafter the terminating ends of the capillary columns cut in the prescribed length are successively dropped between planes and arranged in a line by the arrangement means formed by two planes having a parallel clearance slightly wider than the capillary column outer diameter.

A capillary cassette according to the present invention for attaining the third object is such a one that a plurality of capillary columns are fixed by a holder on sample injection sides and planarly arranged in a line on detection sides, coats of the capillary columns are removed so that strip detection windows extending in the capillary column arrangement direction are formed on the capillary column arrangement on the detection sides, the capillary columns adhere to each other and the coats fuse to each other so that the capillary column arrangement is integrated around the detection windows.

In this capillary cassette, the capillary columns adhere to each other, the coats fuse to each other and the capillary column arrangement is integrated around the detection windows, whereby the detection windows planarly align, the focus of an optical system in detection does not deviate, and it is possible to perform correct detection.

When manufacturing the capillary cassette, a manufacturing method according to the present invention forms the detection windows including the following steps (A) and (B):

(A) a step of fixing the sample injection sides of the capillary columns using the holder and thereafter arranging and holding the capillary columns in a line planarly in close contact with each other, and (B) a step of bringing heating means having a length for a plurality of capillary column outer diameters into contact with or approximating the same to a detection window formation planned region of the held capillary column arrangement for removing coats of the plurality of capillary columns while melting the coats around regions from which the coats are removed and thereafter solidifying the same for making the coats of the adjacent capillary columns fuse to each other.

It planarly arranges and fixes the capillary columns not subjected to coat removal of detection parts in a line and simultaneously performs coat removal of detection window formation planned positions of the plurality of capillary columns with the heating means. By simultaneously heating and removing the coats of the plurality of capillary columns, the adjacent capillary columns are fused and integrated with each other on positions separate from the regions from which the coats are removed when the melted coats are cooled and solidified. Thus, the plurality of capillary columns arranged in a line form a flat cable.

For a means of heating, a nichrome wire heater or a ceramic heater can be employed.

When using as the heating means employed for removing the coats that whose length is shorter than the width of the capillary column arrangement on the detection sides, it repeats the step (B) a number of times in the width direction of the capillary column arrangement for forming the detection windows.

This manufacturing method planarly arranges the plurality of columns and thereafter simultaneously removes the coats of the detection parts of the plurality of capillary columns, whereby remarkable reduction of the detection window preparation time can be made as compared with the case of removing the coat as to every single capillary collar.

In the peripheral parts of the detection windows formed by this manufacturing method, the coats melted but not come to be removed fuse the adjacent capillary columns when cooled and solidified. The plurality of fused capillary columns are previously planarly arranged and hence come to planarly maintain the detection windows after fusion, and it is possible to readily manufacture a capillary cassette capable of performing correct optical detection.

When fixing the detection sides of the plurality of capillary columns, it saves trouble of fixing the same one by one while it does not fix the same with an adhesive, whereby a time for drying the adhesive can also be saved.

A gel charging apparatus according to the present invention for attaining the fourth object is an apparatus for charging gels into capillary columns of a capillary cassette. In the capillary cassette, end portions of sample injection sides of a plurality of capillary columns mounted on a multi-capillary electrophoretic apparatus are two-dimensionally arranged while passing through a holding member of a holder and fixed while keeping airtightness between the same and the holding member.

Gel charging into the capillary columns can be performed either by suction or pressurization. In gel charging, it does not seal the respective capillary columns one by one to perform suction or pressurization but seals all capillary columns of the capillary cassette by the holder fixing the capillary columns while keeping airtightness to simultaneously perform gel charging.

In the system performing gel charging by suction, the present invention comprises a chamber provided with an opening in its upper surface so that closure means introducing end portions on sample injection sides of the capillary columns inside and closing the opening with the holder is provided in the opening and further provided with an exhaust port and a release port to the atmosphere, a gel vessel storing a gel solution so that end portions of the capillary columns opposite to the sample injection sides are dipped therein, exhaust means provided on the exhaust port of the chamber, and a switching valve provided on the release port.

When performing gel charging by suction, it dips the forward ends of the detection sides of all capillary columns of the capillary cassette in gels contained in the gel vessel, closes the opening of the chamber with the holder for the capillary cassette, decompresses the chamber with the exhaust means and inhales the gel solution into the capillary columns.

In the system performing gel charging by pressurization, the present invention comprises a chamber provided with an opening on its upper surface so that closure means introducing end portions of the sample injection sides of the capillary columns inside and closing the opening with the holder is provided in the opening while storing a gel solution on such a position that the end portions on the sample injection sides of the capillary columns are dipped therein in such a state that the opening is closed with the holder and further provided with a pressurization port and a release port to the atmosphere, pressurization means provided on the pressurization port of the chamber and a switching valve provided on the release port.

When performing gel charging by pressurization, it introduces the gel solution into the chamber, dips the forward ends of the capillary columns on the sample injection sides in the gel solution, closes the opening of the chamber with the holder, pressurizes the chamber with the pressurization means and pressure-fits gels into the capillary columns.

When charging the gel solution into the plurality of capillary columns forming a capillary array mounted on a multi-capillary electrophoretic apparatus, it does not directly close/fix the respective capillary columns but seals the plurality of capillary columns to the closure means with the sample injection side holder fixing the same with excellent airtightness to perform charging of the gels, whereby gel charging for the plurality of capillary columns can be simultaneously performed. Furthermore, simple mounting and airtightness in mounting can be compatibly attained.

Charging of the gel solution into the plurality of capillary columns can be simultaneously performed, whereby it does not damage the maximum merit of improvement of throughput by simultaneous performance of migration of a plurality of samples in multi-capillary electrophoresis in the process of gel preparation which is the pretreatment thereof.

It is preferable that a flow control valve controlling the flow rate is provided between the release port of the chamber and the switching valve. While the pressure in the chamber is released to the atmosphere after gel charging into the capillary columns, the speed at which the internal pressure of the chamber returns can be controlled with the flow control valve. While air may be mixed into the gels charged into the capillary columns when the degree of decompression or pressurization in the chamber is large, the degree of decompression or pressurization can be controlled with the flow control valve in this case.

In the system performing gel charging by pressurization, the gel 15 solution may be directly introduced into the chamber, while it is preferable in the aspect of maintenance of the chamber when providing an attachable/detachable vessel in the chamber for storing the gel solution in the vessel.

BRIEF DESCRIPTION OF THE DRAWINGS

FIG. 4 is a top plan view of the capillary cassette of the embodiment.

FIG. 5 shows diagrams mounting a carrier on the embodiment, (A) is a front elevational view, (B) is a left side elevational view, and (C) is a top plan view.

BEST MODES FOR CARRYING OUT THE INVENTION

Figure 1:
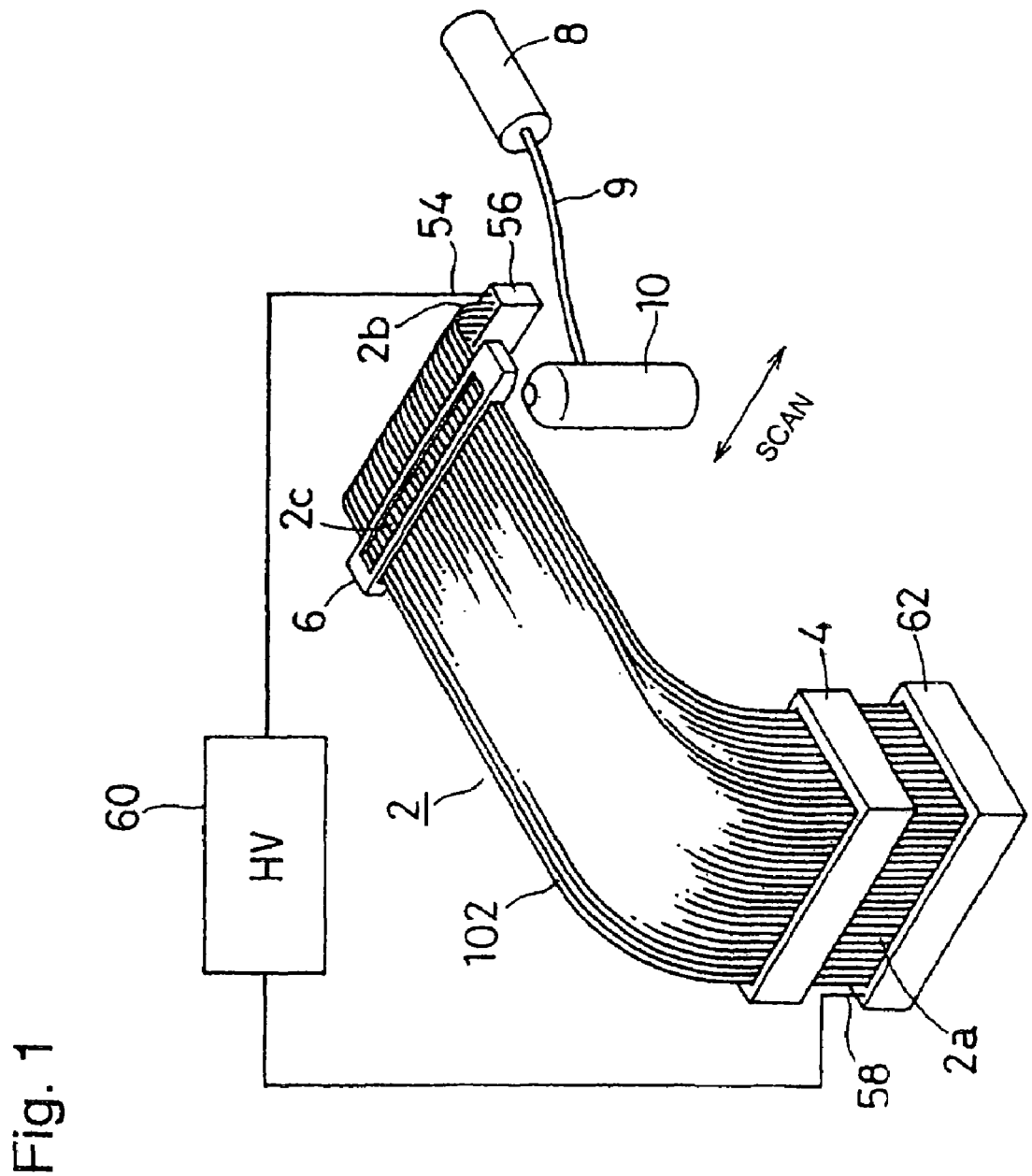
FIG. 1 is a schematic perspective view showing an example of a multi-capillary electrophoretic apparatus to which a capillary cassette according to the present invention is applied.

FIG. 1 shows a schematic perspective view of an example of a multi-capillary electrophoretic apparatus to which a multi-capillary cassette according to the present invention is applied.

A capillary cassette 2 is such a one that a plurality of capillary columns 102 are arranged and fixed by holders 4 and 6 to form a capillary array, and an end 2a of the capillary array defines a sample injection side and is two-dimensionally arranged and fixed by the holder 4, to come into contact with a buffer solution of a reservoir 62 for migration after sample injection. A terminating end 2b of the capillary array is such that the capillary columns 102 are arranged in a line on a plane, to come into contact with a buffer solution of a reservoir 56 on the forward end. Such a detected portion 2c that the capillary columns 102 are arranged in a line and supported by the holder 6 is provided on a terminating end side (detection side) of the capillary array. The capillary columns 102 are coated with coats to be protected against breakage. When a fluorescent detection method is employed for detecting migrating samples and if the coats emit fluorescence, it removes the coats on the detected portion 2c. When using those coated with coats which are transparent and made of a non-fluorescent material, the coats of 102 of the capillary columns do not have be removed also on the detected portion 2c. A number of capillary columns, e.g., 384 capillary columns are arranged on the capillary cassette 2.

Different samples are injected into the respective capillary columns 102, and electrophoresis is simultaneously performed.

For an excitation light source 8 to be used for exciting the samples themselves or fluorescent materials labeling the samples, an argon gas laser unit, for example, is provided. 10 is an excitation•photoreceiving optical system, which is that irradiating the capillary columns 102 of the detected portion 2c with excitation light and detecting fluorescence from the samples, and scanned by a scanning mechanism (illustration omitted) in a scan direction parallel to the arrangement plane of the capillary cassette in the detected portion 2c and perpendicular to a migration direction. In order to make the excitation light beam from the excitation light source 8 not deviate even by scanning of the excitation•photoreceiving optical system 10, the laser beam from the excitation light source 8 is guided to the excitation•photoreceiving optical system 10 through optical fiber 9 coupled by a coupler here as an example.

A migration buffer solution is contained in the lower reservoir 62, the lower end 2a of the capillary array is dipped in the buffer solution, and a migration voltage is applied to the capillary ends of the lower end 2a of the capillary cassette 2 through the buffer solution. An upper electrode 54 is dipped in and comes into contact with the buffer solution of the upper reservoir 56, a lower electrode 58 is dipped in and comes into contact with the buffer solution of the lower reservoir 62, and the migration voltage is applied to both electrodes 54 and 58 from a high pressure power source 60. Its power supply voltage is 30 kV, for example, and a current capacity is 10 to 30 mA.

The migrated samples are protein samples, DNA fragments labeled with a fluorescent material or the like.

Figure 2:
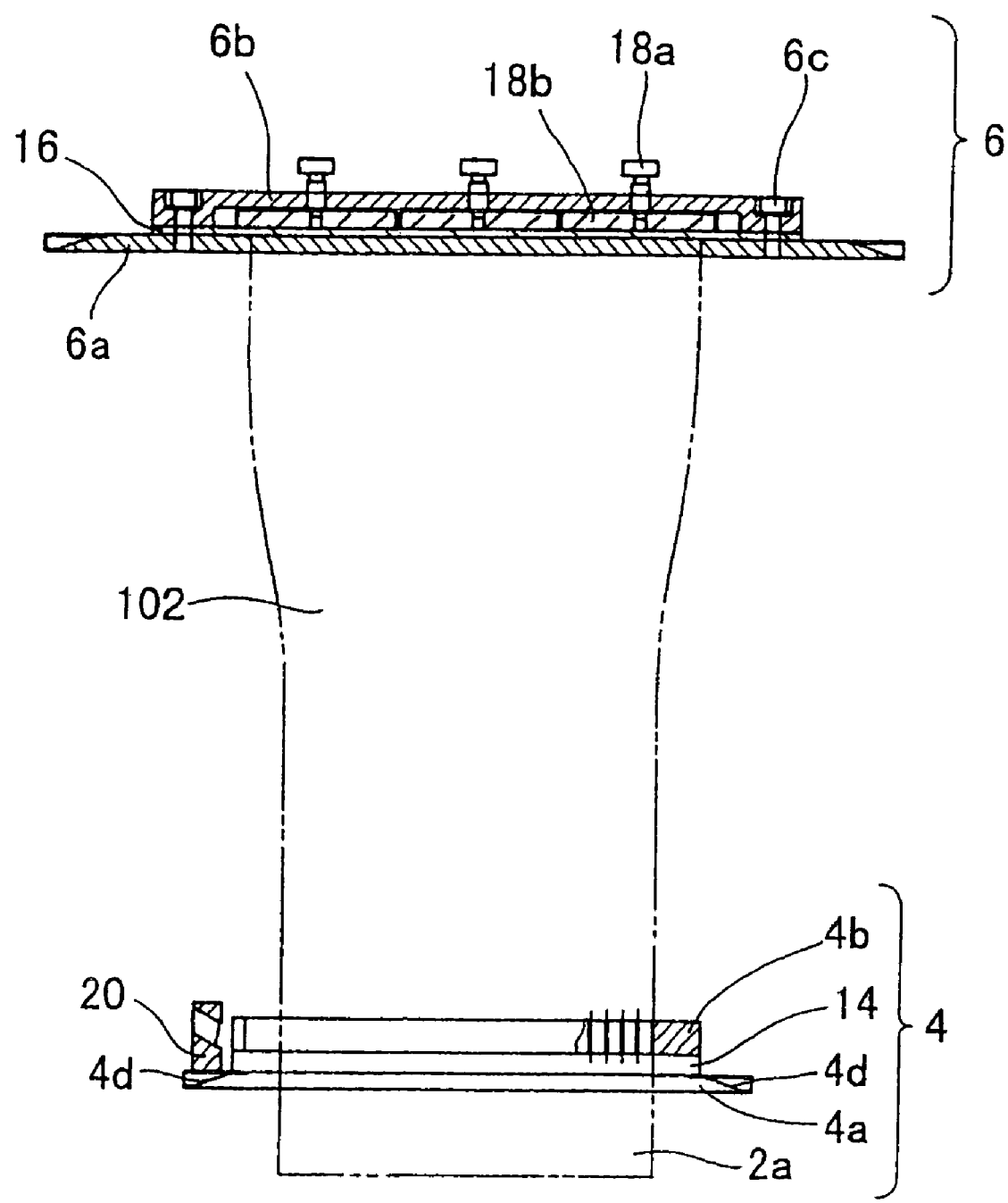
FIG. 2 is a front elevational view of a capillary cassette of one embodiment.
Figure 3:
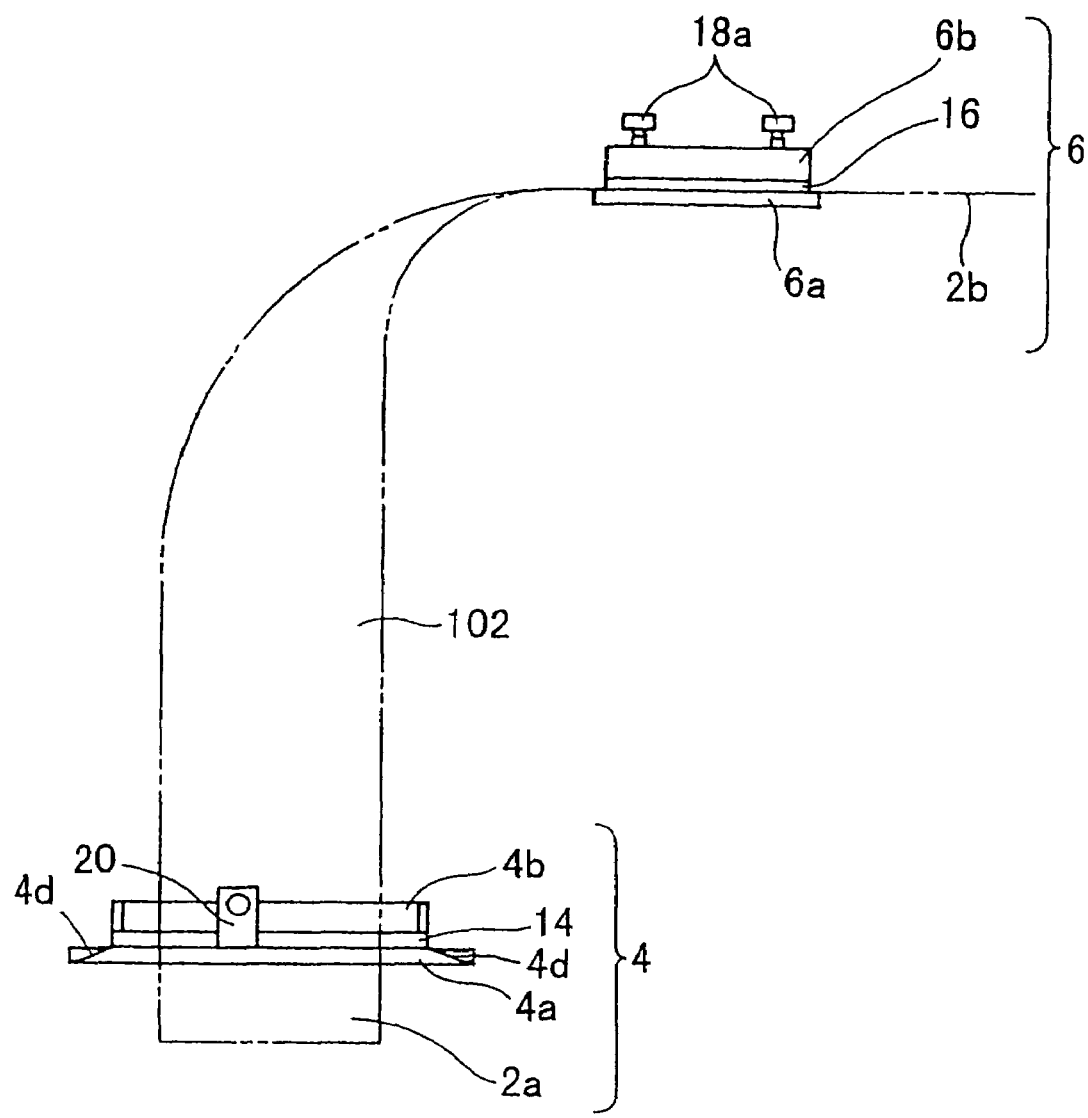
FIG. 3 is a left side elevational view of the capillary cassette of the embodiment.

FIG. 2, FIG. 3 and FIG. 4 show schematic block diagrams of a capillary cassette of one embodiment. FIG. 2 is a front elevational view, FIG. 3 is a left side elevational view, and FIG. 4 is a top plan view. The same reference numerals are assigned to parts playing the same roles as FIG. 1.

A holder 4 on a sample injection side has a coat, and is such a one that a rubber plate 14 made of silicone rubber of 5 mm in thickness holding and fixing capillary columns 102 with a hole is held between holder plates 4a and 4b of resin for two-dimensionally arranging the quartz glass capillary columns 102 of 300 μm in outer diameter and 100 μm in inner diameter, for example, and integrated by fixing screws 4c. 384 holes passing the capillary columns 102 therethrough are provided on both holder plates 4a and 4b in two dimensions of 16 by 24 of 4.5 mm pitches in correspondence to positions of respective holes of a 384-hole microplate used for sample introduction. The holes of the holder plates 4a and 4b are set to be larger than the outer diameters of the capillary columns 102. The capillary columns 102 pass through both holder plates 4a and 4b and the rubber plate 14 held therebetween and are held in the holes of the rubber plate 14 by elasticity of rubber, thereby being fixed while keeping airtightness between the same and the holder 4. A carrier fixture 20 is provided on an end of the holder plate 4a.

A holder 6 on a detection side fixes the capillary columns 102 closely arranged on a plane by holding the same with a holder plate 6a from below and with a rubber plate 16 of silicone of 2 mm in thickness from above. In order to press the capillary columns 102 against the holder 6 with the rubber plate 16 and fix the same, holder plates 6b fixing the rubber plate 16 to the holder plate 6a by fixing screws 6c are provided on both side portions of the arrangement of the capillary columns 102.

When arranging the 384 capillary columns 102 in a line in the holder 6, the width becomes about 12 cm even if arranging the same in close contact, and hence the rubber plate 16 is bent outward at the central portion when fixing both end portions, and hence the force of the rubber plate 16 holding the capillary columns 102 weakens around the center of the holder 6. So that the rubber plate 16 does not float in a direction separating from the holder plate 6a between both end portions at which the rubber plate 16 is fixed to the holder plate 6a by the holder plate 6b, two grooves 17a extending in the arrangement direction of the capillary columns 102 are provided inside (the side opposed to the rubber plate 16) of the holder plate 6b, clamp bars 18b pushing the rubber plate 16 in the direction of the holder plate 6a are engaged in several portions, e.g., in positions of six portions in total including three portions on either side, and a clamp screw 18a fitted with the holder plate 6b to project outward from the holder plate 6b is provided in each clamp bar 18b. By adjusting the clamp screw 18a, clamping force pressing the capillary columns 102 through the rubber plate 16 can be adjusted.

The total length of the capillary columns 102 is about 500 mm, and the detected portion 2c is provided on a position of about 400 mm from a sample injection end. In order to form detection windows on the detected portion 2c, a slot 17c along the arrangement direction of the capillary columns 102 is opened in the holder plates 6a and 6b and the rubber plate 16 to define the detected portion 2c. Signal detection in electrophoresis is performed through the slot 17c.

In order to fix the capillary columns 102 to the holder 4, it holds the rubber plate 16 between the holder plates 4a and 4b, passes the rubber plate 14 with a needle along the opening holes of the holder plate 4b, thereafter inserts the capillary columns 102 into the needle, and extracts only the needle, as described later with reference to FIG. 6 to FIG. 9 in detail.

Thus, the capillary columns 102 pass through the rubber plate 14, and are supported and fixed by the rubber plate 14 in a state held by elastic force of rubber. Thereafter it cuts the capillary columns 102 in a prescribed length. By repeating this operation while changing the positions of the holes of the holder plate 4b, the capillary columns 2 are two-dimensionally arranged and fixed to the holder 4.

In this embodiment, the capillary columns 102 are fixed not only to the holder 4 but also to the holder 6 employing no adhesives. Therefore, the capillary columns 102 are readily separated from the holders 4 and 6, and it is also possible to exchange defective capillary columns.

Also, as described later, a gel charging apparatus according to the present invention is provided with a guide rod 130a guiding the holder 4 and fixing means 111 fixing the holder 4, and the holder 4 is provided with a guide hole 30b through which the guide rod 130a passes and a fixing part 4b so inclined that thickness of four corners reduce toward an outward direction to be engaged with the fixing means 111.

When clamping the holder plate 6b with respect to the holder plate 6a with force beyond necessity in the holder 6 on the detection side, the holder plate 6b is bent due to the combined thickness of the capillary columns and the rubber plate. In order to prevent this, it is preferable to provide a groove in the holder 6b in fixing parts of the holder plates 6a and 6b in response to the thickness of the rubber plate or to insert a spacer between the holder plates 6a and 6b. It is also preferable to prepare the holder plate 6b while previously warping the same opposite to the bent direction. These are effective for preventing the holder plate 6b from being bent, and effective for maintaining the force pressing the rubber plate 16 through the clamp 18 and maintaining holding force around the center of the rubber plate 16.

For carriage of the capillary cassette, it is convenient to use a carrier. FIG. 5 shows a capillary cassette comprising a carrier as an example. (A) is a front elevational view, (B) is a left side elevational view, and (C) is a top plan view.

An end of an L-shaped carrier pipe 22 is fixed to a carrier fixture 20 of a holder 4, a holder fixing part 26 is provided on another end of the carrier pipe 22, and a holder 6 is fixed to the holder fixing part 26 by fixing screws 28. The holders 4 and 6 are fixed by the carrier pipe 22.

In the embodiment of FIG. 5, the carrier 22 is attachable/detachable, and it is possible to mount the carrier 22 and fix the holders 4 and 6 when carrying the capillary cassette and detach the same when mounting the capillary cassette to an electrophoretic apparatus. However, a capillary cassette integrated with a carrier may be prepared to be mounted on an electrophoretic apparatus while comprising the carrier.

Figure 6:
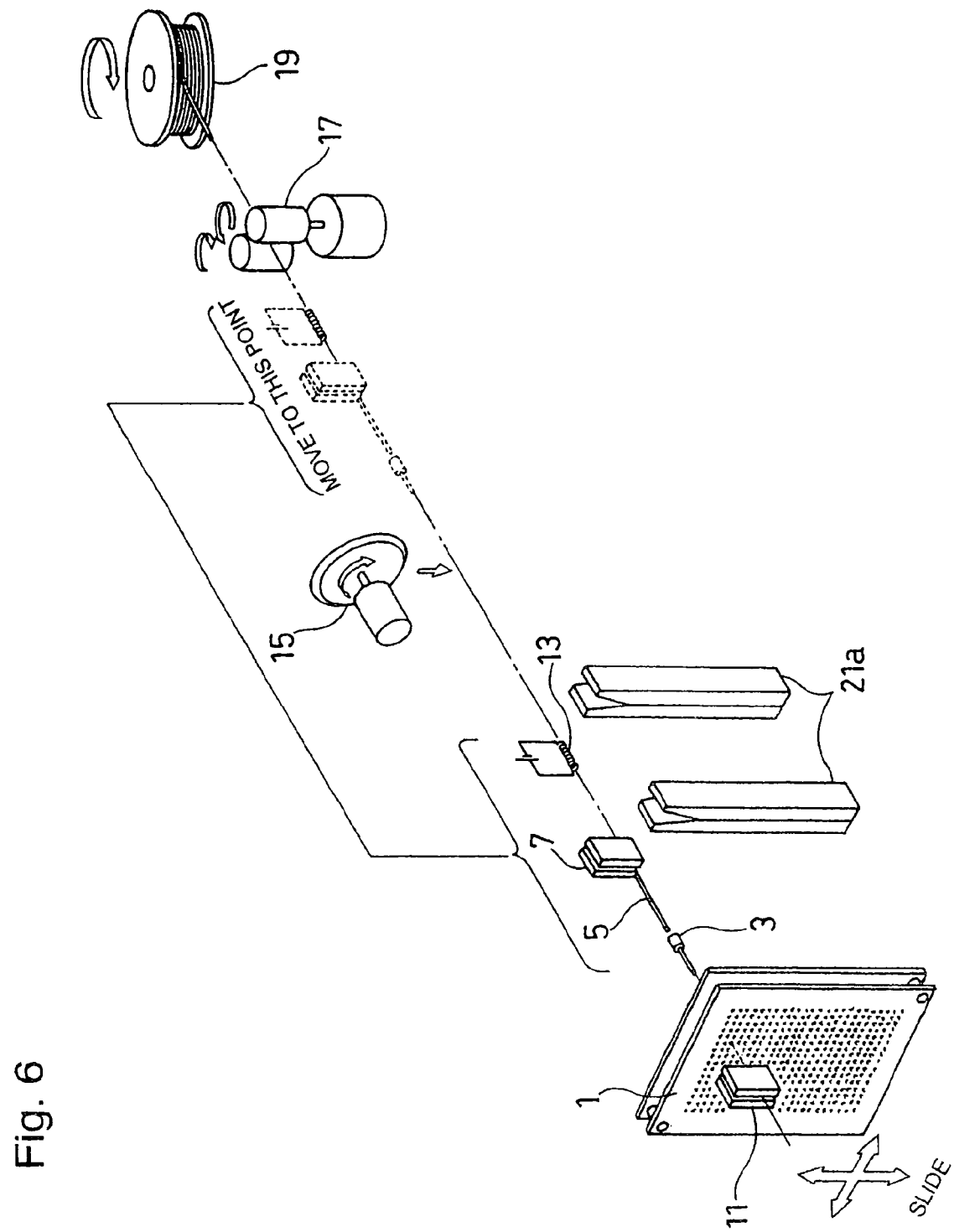
FIG. 6 is a schematic perspective view of one embodiment of a capillary cassette preparation apparatus according to the present invention.

FIG. 6 shows a schematic block perspective view of one embodiment of a capillary cassette preparation apparatus, and an example of a capillary cassette preparation method according to the present invention is described with reference to this.

The embodiment employs quartz glass capillary columns of 300 μm in outer diameter and 100 μm in inner diameter. As a sample injection side holder, it employs a sample injection side holder 1 holding capillaries in two dimensions of 16 by 24 of 4.5 mm pitches in coincidence with a 384-hole microplate used in sample injection.

The sample injection side holder 1 is in such a structure that a supporter consisting of a silicone rubber plate is held between two metal plates or resin plates in which holes are provided on positions matched with the 384-hole microplate. A needle 3 (e.g., 0.72 mm in outer diameter and 0.41 mm in inner diameter) linearly moving in a direction perpendicular to the plane of the supporter and passing through the supporter is provided. The needle 3 has an inner diameter larger than the outer diameter of the capillary columns. A chuck 7 serving as a first capillary column holder chucking prescribed positions from forward ends of the capillary columns and inserting the forward ends into the needle 3 is provided, and a guide pipe 5 having an inner diameter larger than the outer diameter of the capillary columns is provided for guiding the forward ends of the capillary columns chucked by the chuck 7 into the needle 3. In order to hold the forward end portions of the capillary columns made to project from the forward end of the needle 3 in such a state that the needle 3 passes through the supporter, a chuck 11 serving as a second capillary column holder is also provided. Furthermore, a nichrome wire coil 13 preparing detection windows on prescribed positions from the forward ends of the capillary columns is provided. The guide pipe 5, the chuck 7 and the nichrome wire coil 13 move on the same straight line as the needle 3. Furthermore, a cutter 15 cutting the capillary columns whose single end sides are fixed to the sample injection side holder 1 in a prescribed length and a capillary feed 17 drawing out the capillary columns wound on a capillary drum 19 by a constant length are also provided.

It is possible to move the needle 3, the guide pipe 5, the chuck 7 and the nichrome wire coil 13 reciprocally between a position further on the left side of the position where the needle 3 passes through the supporter of the sample injection side holder 1 and a position of broken lines.

The capillary cassette preparation method according to the present invention is formed by the following procedure:

(1) It mounts the sample injection holder 1 on a non-illustrated XY stage holding the sample injection side holder 1 and sliding the same upward, downward, leftward and rightward in the figure while directing the plane of the supporter of the sample injection side holder 1 in a direction perpendicular to the needle 3, and matches a hole provided on the sample injection side holder 1 on the moving straight line of the needle 3. The hole defines a fixing position for the capillary columns.

(2) In the state where the chuck is on the position of the broken lines, it extracts a capillary column from the capillary drum 19 using the capillary feed 17 by the same length as the capillary columns comprised in the capillary cassette. The extracted capillary column is stored between the chuck 7 and the capillary feed 17 in a loosened state.

(3) It passes through the supporter in the sample injection holder 1 by the needle 3.

(4) It presses the capillary column whose prescribed position from forward end is chucked by the chuck 7 in the left direction, to make the forward end pass through the supporter through the guide pipe 5 and the needle 3. When the needle 3 is clogged with sediment of the supporter, it pushes out the same with the capillary column. At this time, the capillary column between the needle 3 and the chuck 7 is protected by the guide pipe 5, whereby it is possible to prevent the capillary column from being bent and broken by the force pressing the sediment of the supporter in the needle 3.

(5) It chucks the forward end of the capillary column passing through the needle 3 and projecting on the opposite side of the sample injection side holder 1 with the chuck 11.

(6) It removes the coat of the capillary column on the prescribed position from the forward end of the capillary column with heat of the nichrome wire coil 13 and prepares a detection window.

(7) It extracts only the needle 3 from the supporter of the sample injection side holder 1. The capillary column passing through the supporter is fixed to the sample injection side holder 1 by elastic force of the supporter acting in a direction closing the hole.

(8) In a state chucking and holding the forward end of the capillary column with the chuck 1, it moves the needle 3, the guide pipe 5, the chuck 7 and the nichrome wire coil 13 while sliding the same in the direction of the capillary feed 17 along the capillary column. Thereafter it cuts the capillary column in a prescribed length from the forward end with the cutter 15.

(9) The cut side (detection side) of the capillary column whose one end is fixed to the sample injection holder 1 is dropped into two slit holders 21a consisting of two planes having parallel clearances slightly wider than the outer diameter (300 µm) of the capillary column, and aligned in cut order, i.e., the order fixed to the sample injection side holder 1.

(10) The XY stage moves so that a next fixing position of the capillary cassette 1 is located on a moving locus of the needle 3.

(11) It repeats (2) to (10) 384 times, fixes the capillary columns to all fixing positions of the capillary cassette 1, thereafter aligns end surfaces of the aligned capillary columns on the detection side with the slit holders 21a, and mounts/fixes the detection side holder.

When executing the capillary cassette preparation method according to the present invention, preparation of a capillary cassette can be simply and quickly performed.

Figure 7:
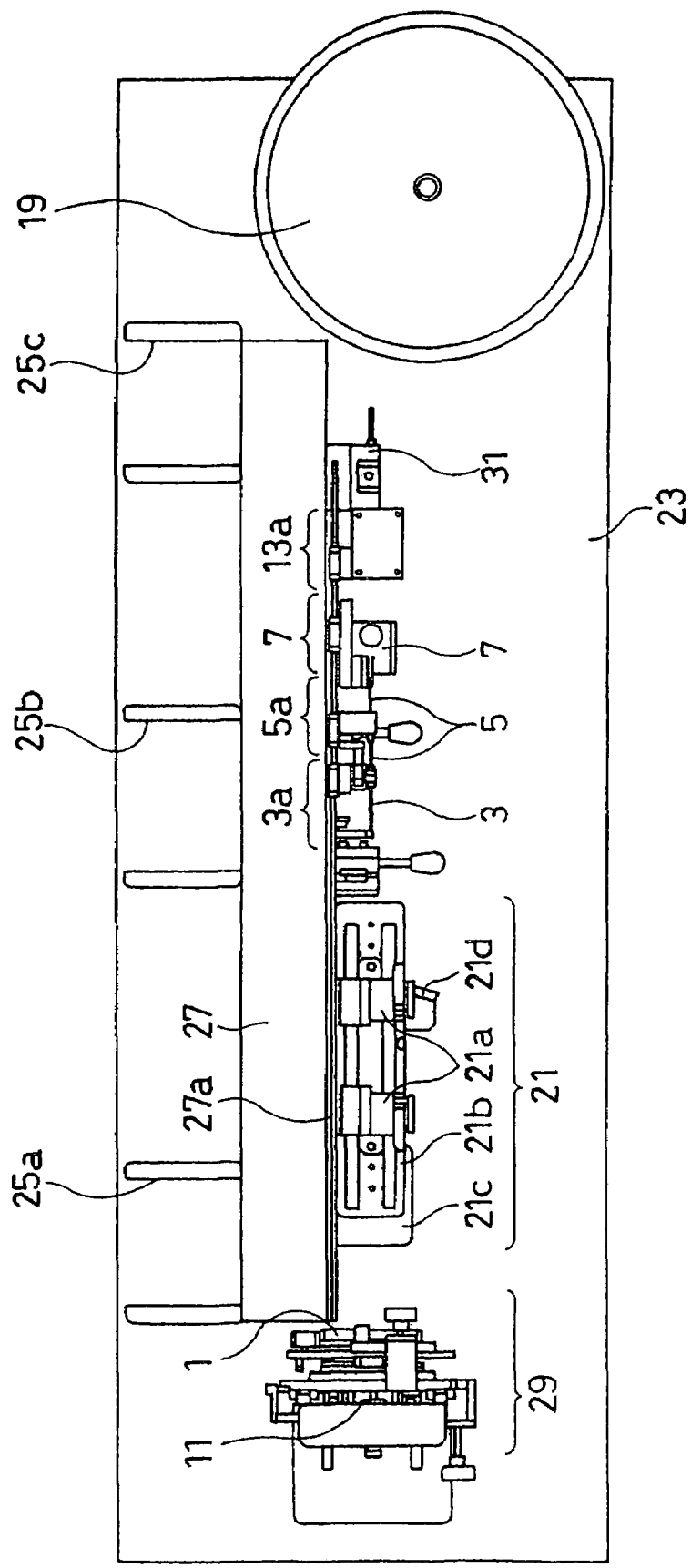
FIG. 7 is a plan view of the embodiment.
Figure 8:
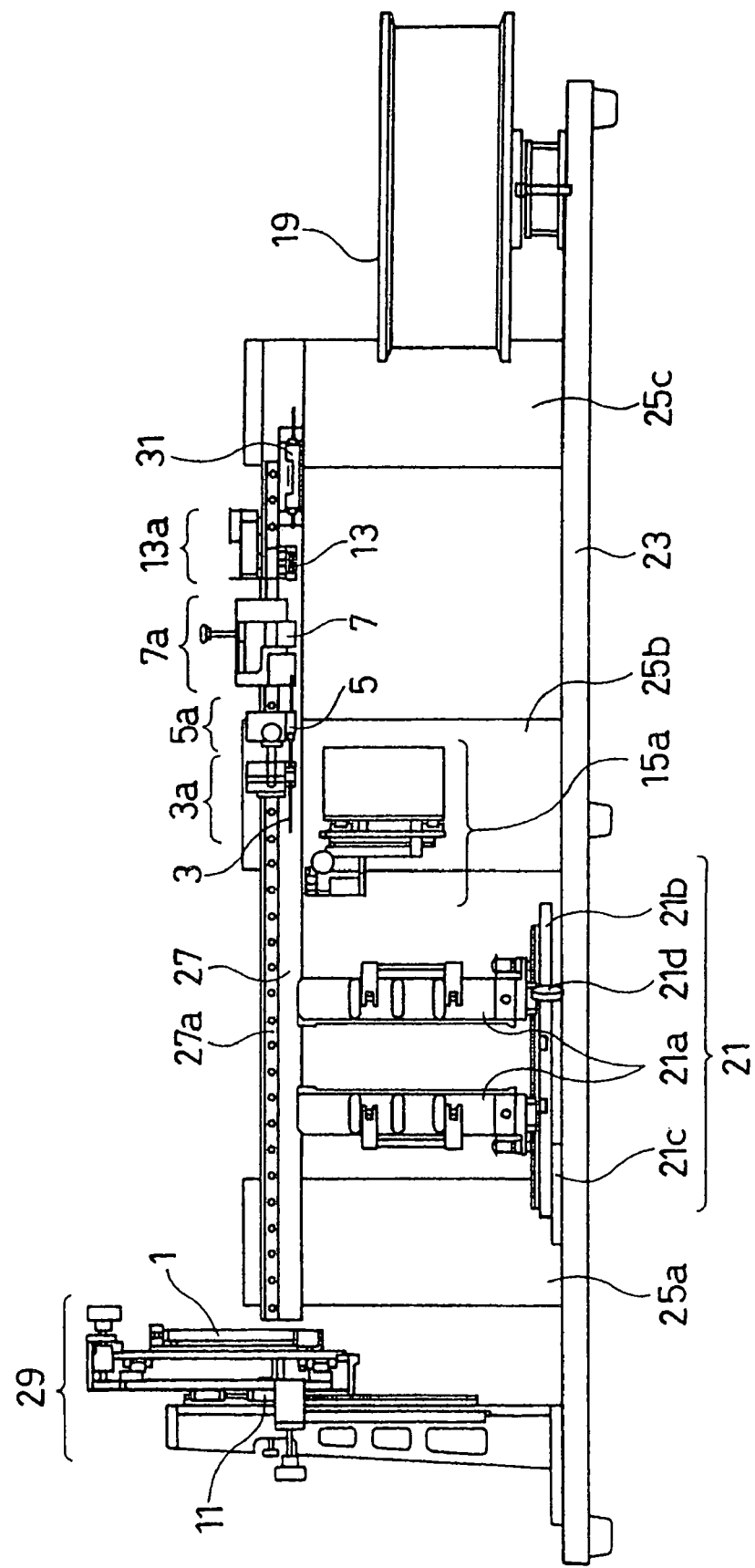
FIG. 8 is a front elevational view of the embodiment.

FIG. 7 and FIG. 8 show block diagrams of one embodiment of a capillary cassette preparation apparatus for more reliably carrying out the aforementioned capillary cassette preparation method. FIG. 7 is a plan view and FIG. 8 is a front elevational view. The same reference numerals are assigned to parts playing the same roles as FIG. 6.

Three struts 25a, 25b and 25c are comprised on a substrate 23 in a direction perpendicular to the plane of the substrate 23. A slide plate 27 comprising a rail 27a sliding a needle unit 3a, a guide unit 5a, a holder unit 7a and a detection window preparation unit 13a described later in a direction parallel to the substrate 23 on its side surface is fixed over the three struts 25a, 25b and 25c. An XY stage is comprised on the substrate 23 on extension of the longitudinal direction of the slide plate 27 with its moving direction (XY plane) along a vertical direction. A sample injection side holder 1 having a silicone rubber plate as a supporter is mounted on the XY stage 29 with the plane of the supporter perpendicular, and it can be moved upward, downward, leftward and rightward. A chuck 11 holding and keeping a forward end of a capillary column is comprised on an opposite side (a side opposite to the slide plate 27) of the XY stage 29 on extension of the longitudinal direction of the slide plate 27.

A needle 3 having an inner diameter larger than the outer diameter of the capillary column and passing through the silicone rubber plate which is the supporter of the sample injection holder 1 is comprised in the needle unit 3a sliding on the rail 27a comprised on the slide plate 27. A guide pipe 5 having an inner diameter larger than the outer diameter of the capillary column for making the capillary column between the needle unit 3a and the holder unit 7a described later not bent is comprised in the guide unit 5a. A chuck 7 chucking a prescribed position from the forward end of the capillary column is comprised in the holder unit 7a. A nichrome wire coil 13 burning and removing a coat of the capillary column is comprised on the detection window preparation unit 13a, and the capillary column passes through the center of the nichrome wire coil 13. A ceramic pipe cutting off transmission of heat from the nichrome wire coil 13 to the capillary column is provided between the capillary column and the nichrome wire coil 13 to be movable along the capillary column. Around the strut 25c on the side surface of the slide plate 27, a pipe unit 31 guiding the capillary column to the holder unit 7a is fixed so that the capillary column fed from a capillary drum 19 described later becomes linear along the slide plate 27.

The chuck 11, the needle 3, the guide pipe 5, the chuck 7 and the nichrome wire coil 13 are provided on a straight line.

The capillary drum 19 winding and storing a single long capillary column is comprised on the substrate 23 on the opposite side to the XY stage.

A cut unit 15a cutting the capillary column after being held by the sample injection side holder 1 in a prescribed length by moving a cutter upward and downward is comprised on the strut 25b.

A detection side cassette preparation unit 21 is provided on the substrate 23 between the strut 25a and the strut 25b, and two slit holders 21a consisting of two planes having parallel clearances slightly wider than the capillary column outer diameter are comprised on a rotary plate 21b provided in parallel with the substrate 23. The rotary plate 21b is in contact with the substrate 23 through a fulcrum plate 21c and a roller 21d, and the longitudinal direction of the rotary plate 21b is fixed in a direction parallel to the slide plate 27 during an operation of fixing the capillary column to the sample injection side holder 1, and the clearances of the slit holders 21a are also directed to the direction parallel to the slide plate 27, i.e., the direction of the XY stage 29 at this time. It is in such a structure that the detection side cassette preparation unit 21 can rotate in the opposite direction to the slide plate 27 by 90° in a direction parallel to the substrate 23 about a non-illustrated rotation axis provided in the fulcrum plate 21c in detection side cassette preparation. By rotating the detection side cassette preparation unit 21 by 90°, the capillary column enters a state bent by 90° as shown in FIG. 1, and is thereafter fixed to the detection side holder.

Figure 9:
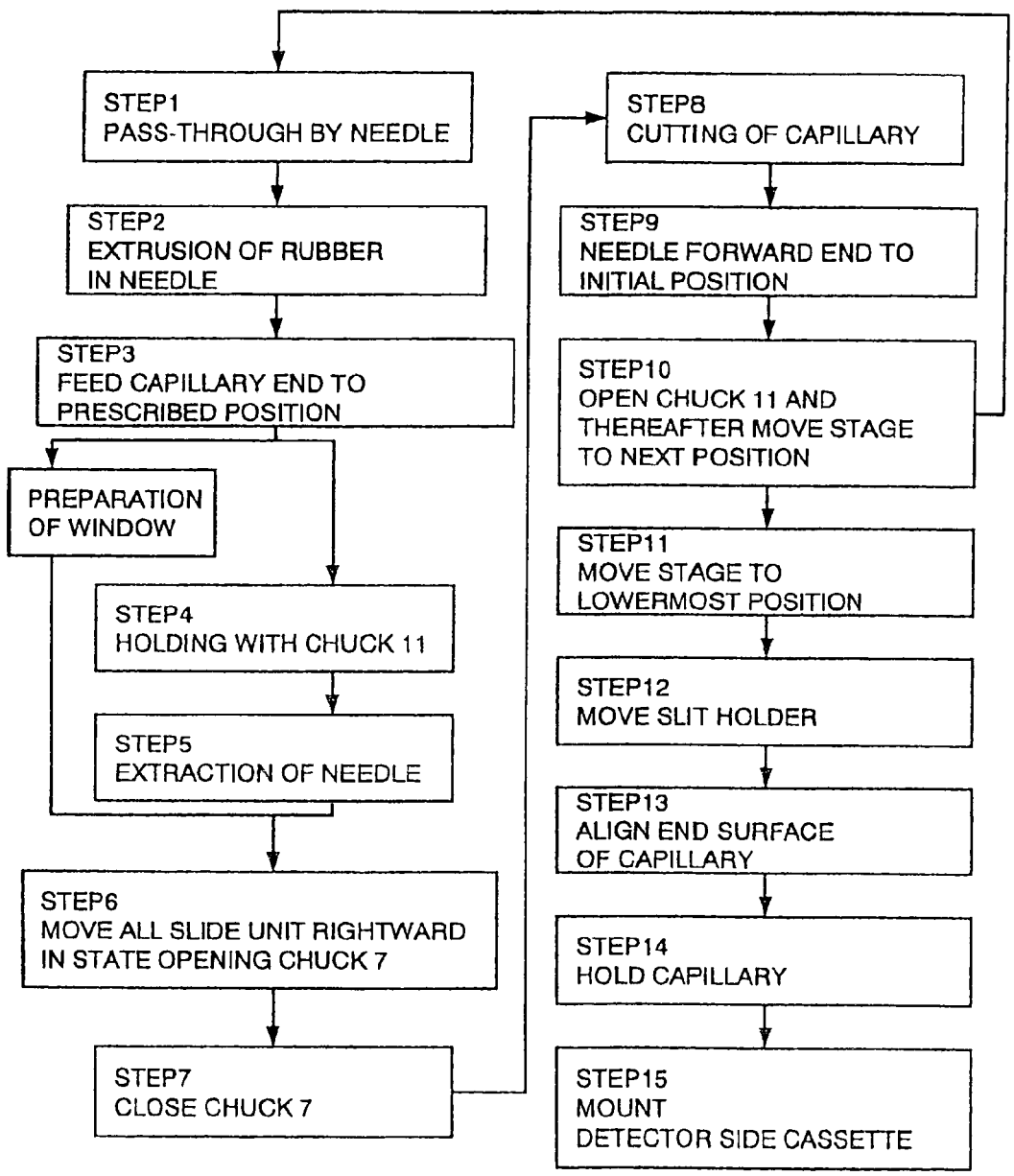
FIG. 9 is a flow chart of the operation procedure of the embodiment.

FIG. 9 shows a flowchart of an operation procedure of the aforementioned embodiment, and description of the operation is made employing FIG. 7 to FIG. 9.

It moves the XY stage and matches a position of the sample injection side holder 1 for first fixing the capillary column on the straight line of the chuck 11, the needle 3, the guide pipe 5, the chuck 7 and the nichrome wire coil 13. The positions of the needle unit 3a, the guide pipe 5a, the holder unit 7a and the detection window preparation unit 13a shown in FIG. 7 and FIG. 8 are initial states. In this state, the forward end of the capillary column wound on the capillary drum 19 is fed to the pipe unit 31 through a non-illustrated capillary feed having a motor for motive power. Furthermore, the forward end is fed into the guide pipe 5 through the nichrome wire coil 13 and the chuck 7, and the capillary column is held and kept by the chuck 7 when the forward end goes out from the guide pipe 5. While the nichrome wire coil 13 is fed with a current and heated, the ceramic pipe intervenes between the nichrome wire coil 13 and the capillary column so that the heat of the nichrome wire coil 13 is not transmitted to the capillary column.

(STEP 1) It moves the needle unit 3a and the guide unit 5a in the left direction with a knob comprised on the guide unit 5a. It moves the needle unit 3a along the rail 27a leftward until the needle 3 sticks into and passes through silicon rubber which is the supporter of the sample injection side holder 1 set on the XY stage 29. At this stage, the holder unit 7a and the detection window preparation unit 13a follow the guide unit 5a while keeping a prescribed space and move along the rail 27a. The capillary column is held by the chuck 7 of the holder unit 7a, to be pulled in the left direction at the same time.

(STEP 2) It moves the guide unit 5a further leftward to bring the same into contact with the needle unit 3a, guides the forward end of the capillary column going out from the guide pipe 5 into the needle 3, makes the forward end of the capillary column project from the forward end of the needle 3, and pushes out sediment of the silicone rubber in the needle 3.

(STEP 3) It moves the holder unit 7a further leftward and makes the forward end of the capillary column further project from the forward end of the needle 3. At this stage, the ceramic pipe between the nichrome wire coil 13 of the detection window preparation unit 13a and the capillary column is moved from the position of the nichrome wire coil 13 on a set time, so that the nichrome wire coil 13 heats a coat on a prescribed position from the forward end of the capillary column and starts preparation of a detection window. Since it requires time for preparation of the detection window, it performs operations of STEP 4 and STEP 5 in parallel.

(STEP 4) It holds the forward end of the capillary column projecting from the forward end of the needle 3 with the chuck 11.

(STEP 5) It moves the needle unit 3a and the guide unit 5a in the right direction until the needle 3 comes out of the silicone rubber, and reduces the space between the same and the holder unit 7a. At this stage, the capillary column is held by the chucks 7 and 11, remains in the state passing through the silicone rubber, and is fixed to the sample injection side holder 1 by elastic force of the silicone rubber.

(STEP 6) It opens the chuck 7, moves the needle unit 3a, the guide unit 5a, the holder unit 7a and the detection window preparation unit 13a rightward, and returns the holder unit 7a and the detection window preparation unit 13a to the positions of the initial states. At this stage, the space between the guide unit 5a and the holder unit 7a is shorter than the initial state.

(STEP 7) The holder unit 7a closes the chuck 7 on the position in the initial state, and holds the capillary column.

(STEP 8) It moves the cut unit 15 upward, and cuts the capillary column with the comprised cutter. The cut portion defines the forward end of a next capillary column. An end of the capillary column cut in the prescribed length is fixed to the sample injection side holder 1, and another end is dropped in the clearance of the slit holders 21a. The capillary column fixed to the sample injection side holder 1 is successively dropped in the clearance of the slit holders 21a, and planarly arranged in a line.

(STEP 9) It moves the needle unit 3a and the guide unit 5a leftward and returns the space between the guide unit 5a and the holder unit 7a to the position in the initial state. Thus, the needle unit 3a, the guide unit 5a, the holder unit 7a and the detection window preparation unit 13a return to the initial positions.

(STEP 10) It opens the chuck 11 and releases the chucked forward end of the capillary column. Thereafter it moves the XY stage and then matches the position of the sample injection side holder 1 for fixing the capillary column on the straight line of the chuck 11, the needle 3, the guide pipe 5, the chuck 7 and the nichrome wire coil 13. When fixation of all capillary columns ends, it advances to STEP 11, otherwise returns to STEP 1.

(STEP 11) It moves the XY stage 29 to the lowermost position for preparing a capillary cassette, and moves the sample injection side holder 1 to a prescribed position.

(STEP 12) In such a state that 384 capillary columns are arranged in a line on a plane in the two slit holders 21a, it rotates the rotary plate 21b of the detection side cassette preparation unit 21 in the opposite direction to the slide plate 27 with a roller 4d by 90° about a non-illustrated rotation axis provided in the fulcrum plate 21c. At this time, each capillary column is bent by 90°.

(STEP 13) It rectilinearly aligns end surfaces of the 384 capillary columns going out from the slit holders 21a with a prescribed jig (angle). At this time, a detection window provided in each capillary column is positioned between the two slit holders 21a.

(STEP 14) It holds and fixes the 384 capillary columns with clamps comprised in the slit holders 11a holding the capillary columns positioned in the clearances of the slit holders 21a.

(STEP 15) It matches the detection side cassette along between the two slit holders 21a and screws the same.

By operating a lever in accordance with the aforementioned procedure, capillary columns of a predetermined length are aligned in set order, so that a capillary cassette can be prepared.

While a manual example has been shown as to the operation in the embodiment, it is preferable to make automatization with a driving source such as a motor or an air cylinder. Thus, preparation of the capillary cassette can be further simply performed without failure.

While the capillary columns have been charged one by one in the embodiment, it is preferable to arrange a plurality of, for example, 16 needles, and capillary columns and simultaneously move the same. Thus, preparation of the capillary cassette in a shorter time can be performed.

Figure 10:
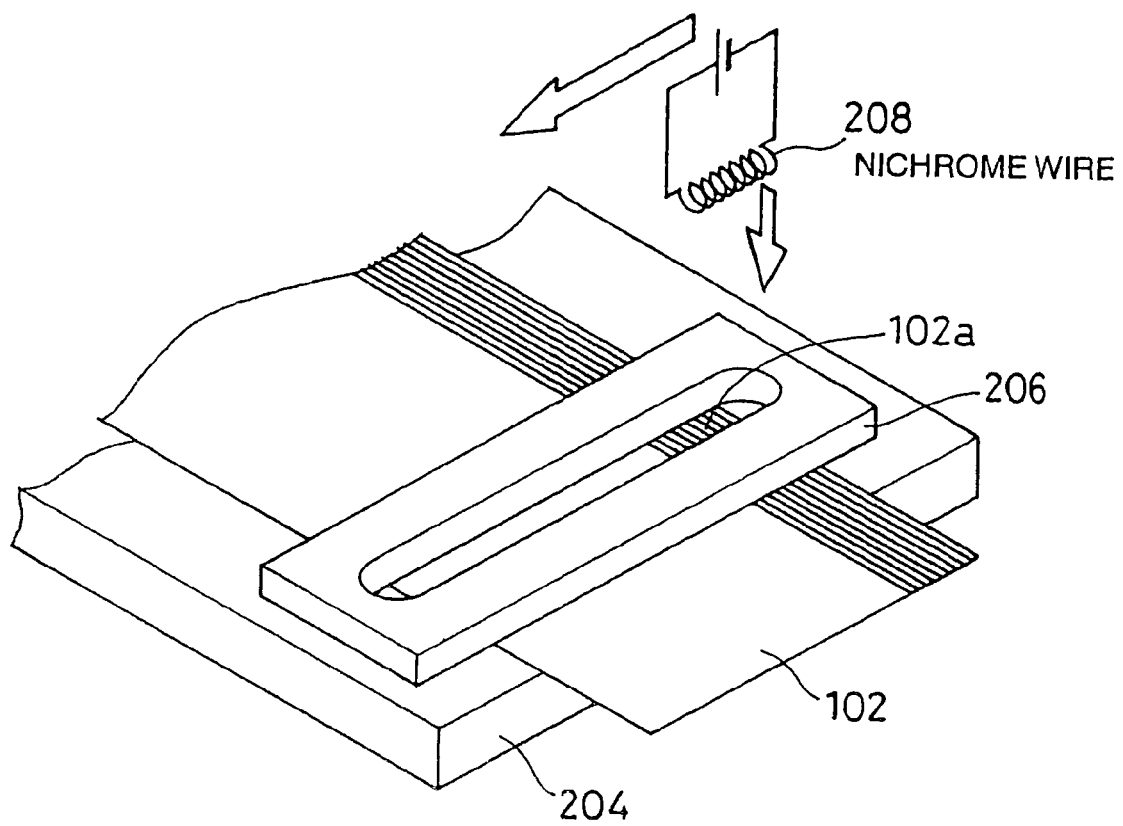
FIG. 10 is a schematic perspective view showing the final step of one embodiment of a capillary cassette manufacturing method according to the present invention.

Another embodiment forming a detection window on the position of a detected portion 2c in a capillary cassette 2 is described with reference to FIG. 10.

(A) After fixing sample injection sides of 384 capillary columns 102 not subjected to coat removal with a holder, it aligns other end sides, i.e., detection sides in a line on the planar of a flat plate 204 in a close contact manner. A slit longer than the arrangement width of the capillary columns 102 is opened in the flat plate 204 in order to prevent the capillary columns 102 from adhering to the flat plate 204 by melting of coats through a coat removal operation, and it performs positioning so that a detection window formation planned region 102a comes onto the slit.

(B) It further overlaps another flat plate 206 on the capillary columns 102. A slot longer than the arrangement width of the capillary columns 102 is opened also in the flat plate 206, and it performs positioning so that the slot comes to the detection window formation planned region 102. Thus, it holds and fixes the capillary columns 102 between the two flat plates 204 and 206.

(C) It feeds a current to a nichrome wire coil 208 to burn the coats and makes it heat red. The nichrome wire coil 208 is that winding a 40 cm long of a nichrome wire of 0.5 mm in diameter, wound into the form of a coil of about 3 mm in diameter and 2 cm in length. The energization quantity is, for example, 5 A.

It brings the red-heating nichrome wire coil 208 into contact with the capillary columns 102 while directing the same to an end portion of the detection window formation planned region 102a through the slit of the flat plate 206 so that the longitudinal direction of the nichrome wire coil 108 is along the arrangement direction (the direction perpendicular to the longitudinal direction of the capillary columns 102) of the capillary columns 102.

(D) It brings the nichrome wire coil 208 into contact with the capillary columns 102 for about 10 seconds, burns and removes the coats on the positions, and thereafter moves the nichrome wire coil 208 along the slot of the flat plate 208 toward the other end portion direction of the detection window formation planned region 102a while partially overlapping portions for bringing the nichrome wire coil 208 into contact so that the coats do not remain on the detection window formation planned region 102a. At this time, coats on surfaces opposite to the surfaces with which the nichrome wire coil 208 comes into contact are also burned and removed.

When the coats of the respective capillary columns 102 melted in positions separate from the nichrome wire coil 208 in burning are cooled and solidified, the adjacent capillary columns 102 are fused to each other by the coats once melted. Thus, the overall plurality capillary columns 102 arranged in a line form a flat cable.

While the embodiment has used the coiled nichrome wire as a means of heating, a long and narrow ceramic heater or the like can also be used as the heating means. When the number of the capillary columns fixed to the holder is large, the width when planarly aligning the capillary columns in a line becomes large. When lengthening the nichrome wire coil for reducing the time required for removal of the coats, its strength weakens in such a manner that the nichrome wire coil is bent and deformed while preparing a detection window by pressing the same against the capillary columns and cannot indeed come into contact with the planarly aligned capillary columns, and it may become necessary to repeatedly perform the burning operation over and over. When using a ceramic heater longer than the width when planarly aligning the capillary columns in a line in such a case, it is possible to form a detection window at once and hence the detection window forming time can be reduced.

Figure 11:
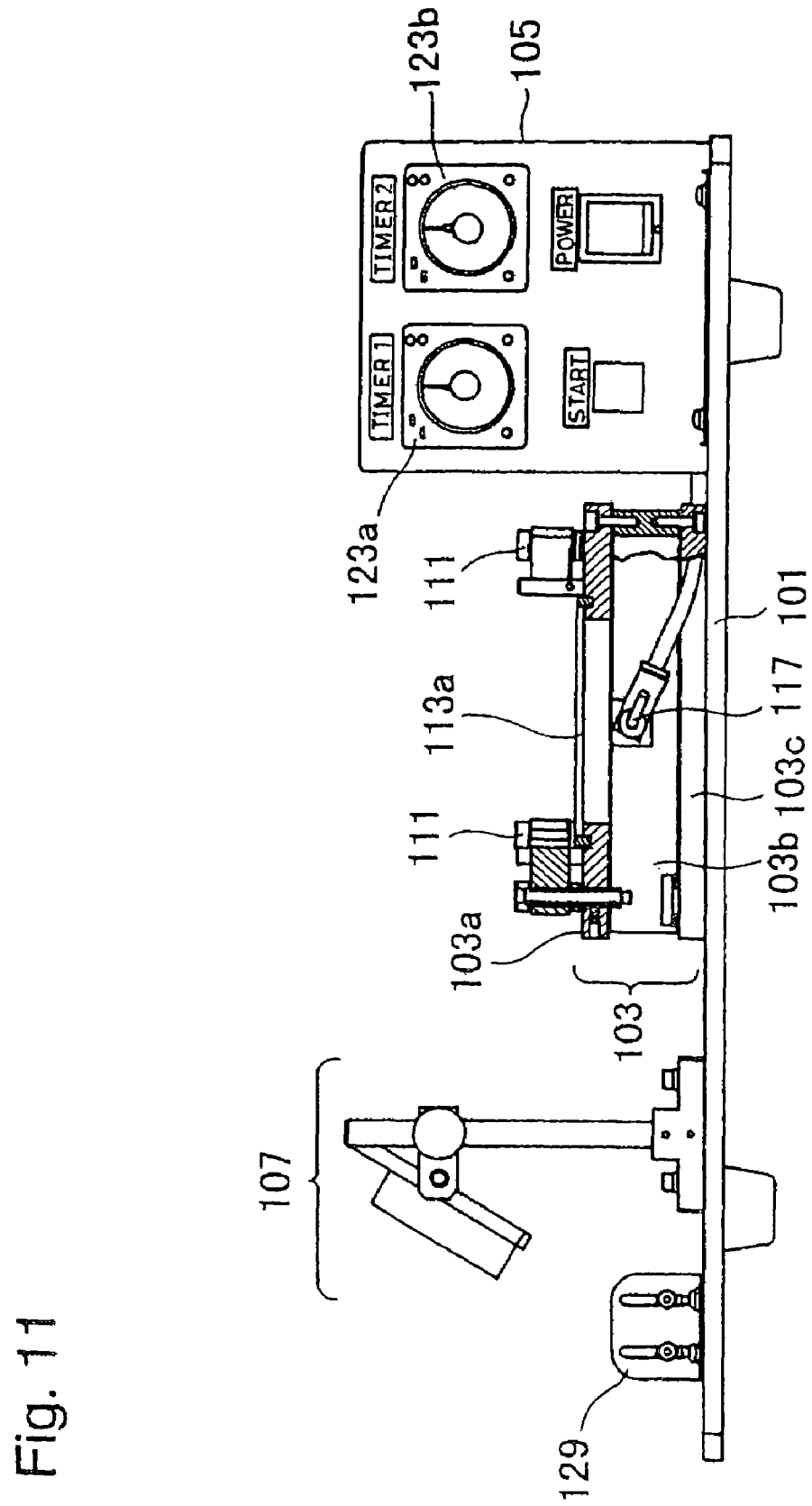
FIG. 11 is a front elevational view showing a schematic structure of one embodiment of a capillary column gel charging apparatus according to the present invention in a partially fragmented manner.
Figure 12:
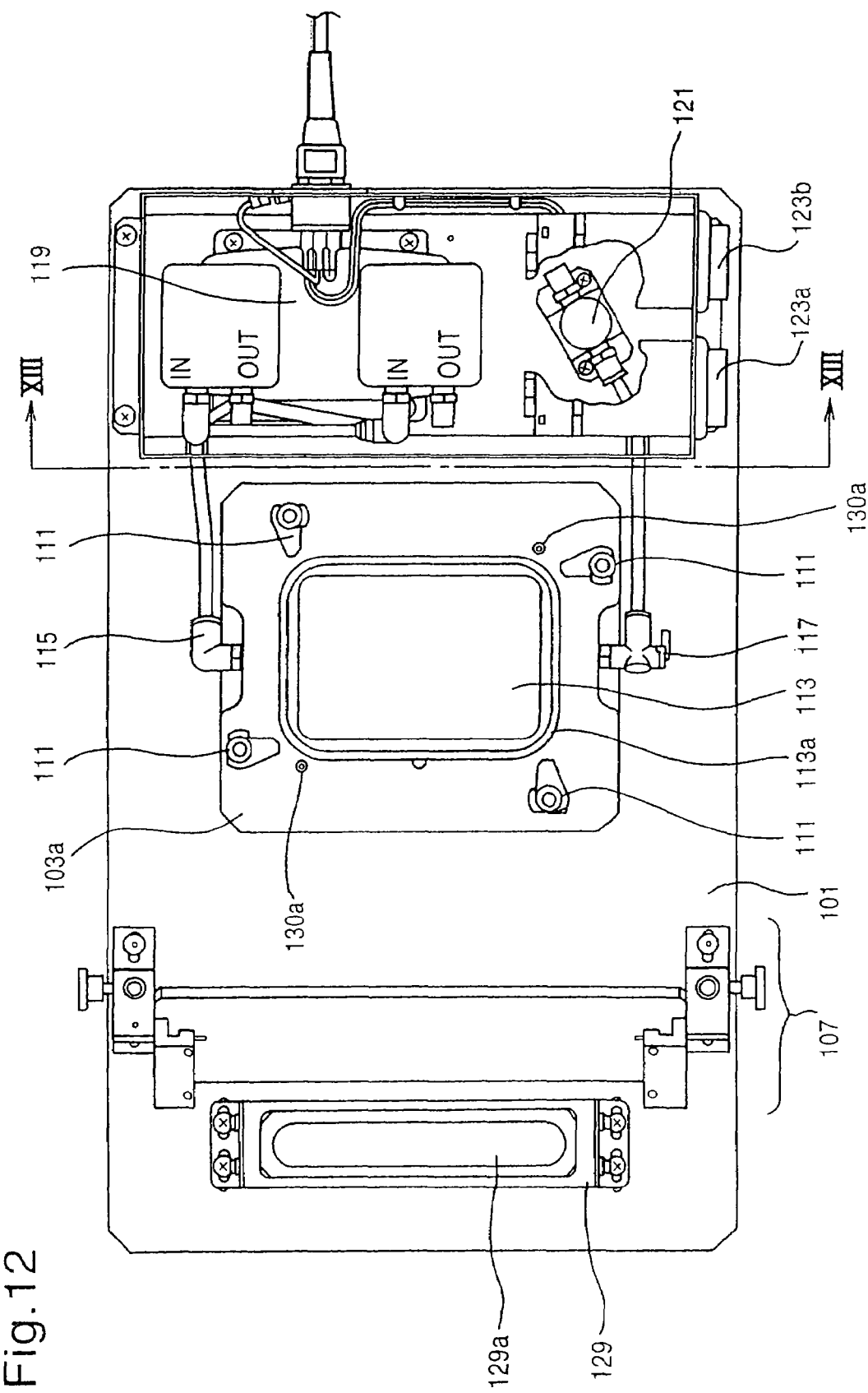
FIG. 12 is a plan view showing the embodiment in a partially fragmented manner.
Figure 13:
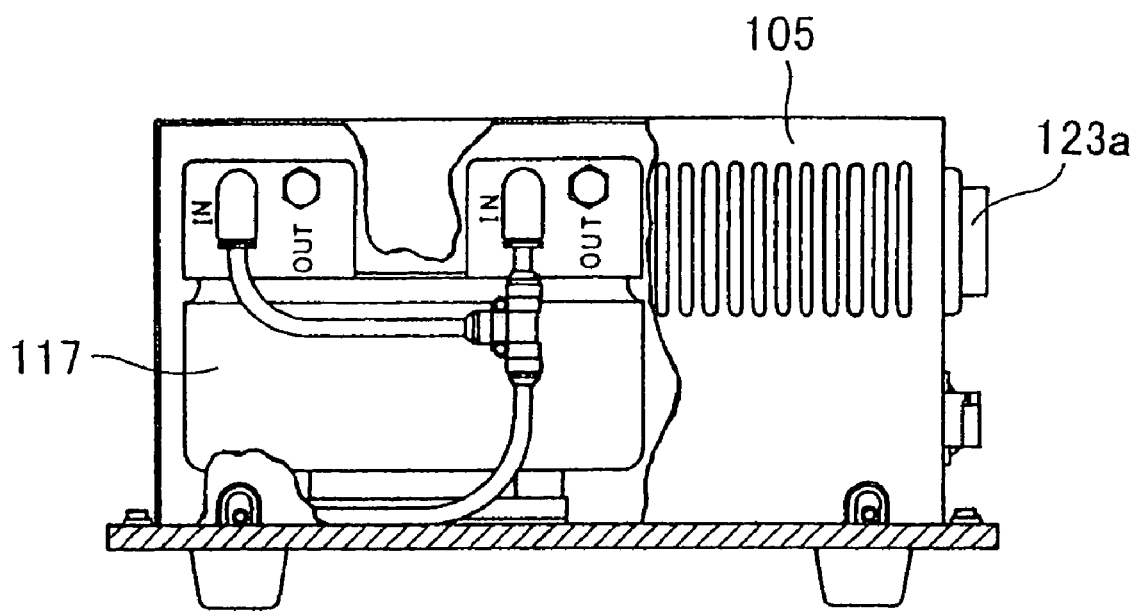
FIG. 13 is a sectional view showing the embodiment in a partially fragmented manner, and that showing a state cut on an A-A line position of FIG. 12.

FIG. 11, FIG. 12 and FIG. 13 show schematic block diagrams of one embodiment of a capillary gel charging apparatus according to the present invention. FIG. 11 is a front elevational view showing a closing means part and a fixing means part in a partially fragmented manner, FIG. 12 is a plan view showing an upper portion of a pump means storage box and a timer unit set therein in a partially fragmented manner, and FIG. 13 is a sectional view showing the pump means storage box in a partially fragmented manner, showing the same while cutting the same along an A-A line position of FIG. 12.

A chamber 103 in which the sample injection side holder 4 shown in FIG. 2, FIG. 3 and FIG. 4 is fixed to form a closed space, a pump means storage box 105 comprising pump means pressurizing or decompressing the chamber 103 therein, detection side holder fixing means 107 and detection side gel vessel fixing means 129 are comprised on a substrate 101.

The chamber 103 is formed by 170 mm×170 mm square acrylic plates 103a and 103c of 10 mm in thickness for closing an upper portion and a bottom portion, and an acrylic pipe 103b of 165 mm in outer diameter and 145 mm in inner diameter for closing side portions. Clearances between both ends of the acrylic pipe 103b and the acrylic plates 103a and 103c are sealed through a silicone rubber packing. An opening 113 of a rectangular hole of 80 mm by 115 mm is provided on the acrylic plate 103, and the sample injection side holder 4 is mounted thereon. A groove is dug around the rectangular hole opening 113, and an annular silicone sponge 113a having a circular section is fit into the groove. About half the silicone sponge 113a goes out from the surface of the acrylic plate 103a, to seal a clearance between the acrylic plate 103a and the sample injection side holder 4. Four clamps 111 for fixing the sample injection side holder 4 to the acrylic plate 103a are comprised on the acrylic plate 103a and engage with fixing parts 4d on four corners of the sample injection holder 4, so that the holder 4 is pressed against the sponge 113a and closes the space of the chamber 103 by tightening the clamps 111.

Two joints are provided on a side surface (cylindrical surface) of the acrylic pipe 103, and a pump 119 pressurizing or decompressing the chamber 103 is connected to one joint 115. An electromagnetic valve 121 releasing the pressure in the pressurized or decompressed chamber 103 to the atmospheric pressure through a needle valve 117 is connected to the other joint, and its return pressure speed is adjusted by the needle valve 117.

In the pump means storage box 105, a timer 123a controlling a working time of the pump 119 and a timer 123b controlling a working time of the electromagnetic valve 121 are stored in addition to the pump 119 and the electromagnetic valve 121.

A detection side gel vessel 129 storing a gel solution when inhaling the gel solution from the detection side is comprised in the detection side gel vessel fixing means 129. It uses a polyacrylamide solution of 5% T and 5% C, for example, for the gel solution.

The operation shall now be described. The embodiment has employed the capillary cassette comprising the 384 capillary columns 102 shown in FIG. 2, FIG. 3 and FIG. 4.

Sample injection sides of the 384 capillary columns 102 are arranged in two dimensions of 16 by 24 of 4.5 mm pitches in coincidence with a commercially available microplate by the sample injection holder 4 and fixed with excellent airtightness, and detection sides thereof are planarly closely fixed in a line by the detection side holder 6.

When performing gel charging by decompressing the chamber 3, it stores the gel solution in a detection side gel vessel 129a. It fixes the fixing parts 4d on the four corners of the detection side holder 4 by the four clamps 111 provided on the acrylic plate 103a so that the forward ends on the detection sides of the capillary columns 102 are dipped into the gel solution stored in the detection side gel vessel 129a, presses the sample injection side holder 4 against the silicone sponge 113a by tightening the clamps 111, and closely fixes the same to the acrylic plate 103a. It decompresses the chamber 103 with the pump 119 for decompressing the inner parts of the capillary columns 102, and inhales the gel solution from the forward ends on the detection sides. The gel solution is charged into the capillary columns 102, and it is preferable to comprise a non-illustrated vessel in the chamber 103 to receive an excess amount of gel solution overflowing from the sample injection side.

When performing gel charging by pressurizing the inner part of the chamber 103, it comprises a non-illustrated vessel storing the gel solution and vacates the vessel 129a. It adjusts the length of the capillary columns projecting from the holder 4 and the height of the vessel storing the gel solution so that the forward ends of all capillary columns on the sample injection side are dipped into the gel solution when fixing the fixing parts 4d on the four corners of the sample injection side holder 4 with the four clamps 111 provided on the acrylic plate 103a. It fixes the detection side holder 6 to the detection side holder fixing means 107. In this case, the sample injection side holder 4 is pressed against the silicone sponge 113 by tightening the clamps 111 and closely fixed to the acrylic plate 103a, so that the space inside the chamber 103 enclosed with the sample injection side holder 4, the acrylic plates 103a and 103b and the acrylic pipe 103 is closed. It pressurizes the chamber 103 with the pump 119 and pushes the gel solution into the capillary columns by the pressure. The gel solution is charged into the capillary columns 102, and it receives an excess amount of gel solution overflowing from the detection side by the detection side gel vessel 129a.

Both in the case of performing decompression and, in the case of performing pressurization, it times the time when the gel solution is charged into all capillary columns 102 and previously sets the working times of the pump 119 and the electromagnetic valve 121 with the timers 123a and 123b. When charging of the gel solution is started by a RUN button, the pump 119 starts working and the chamber 103 is decompressed or pressurized. Continuing the decompression or the pressurization by the time set at the timer 123a, the pump 119 stops at a prescribed time. The inner part of the chamber 103 is still decompressed or pressurized even if the pump 119 stops, whereby the electromagnetic valve 121 opens when the time set at the timer 123b elapses so that the pressure in the chamber 103 is released to the atmosphere through the needle valve 117. At this time, the speed at which the internal pressure of the chamber 103 returns is adjusted by the needle valve 117.

Decompression•pressurization in the chamber 103 can be selected depending on to which one of an exhaust port and a suction port of the pump 119 a pipe connected to the joint 115 is connected.

In order to prevent air from being mixed into the gel charged into the capillary columns since the degree of decompression or pressurization of the chamber 103 is large, it is preferable to control the degree of decompression or pressurization. This control can be performed by a throttle comprised in the needle valve 117 while opening the electromagnetic valve 121 also when the pump 119 operates by the timer 123a. In this case, the electromagnetic valve 121 temporarily closes when the set time of the timer 123a elapses, and opens again after a lapse of the time set in the timer 123b to release the chamber 103 to the atmosphere.

While it is of a pump storing type in the embodiment, it is preferable to render a pressure generation source outside and connect the same to, for example, a high pressure cylinder or a vacuum pump, when the charged gel solution is that having high viscosity such as a flow gel, and it is necessary to generate a high pressure. When employing a high pressure cylinder, it is preferable to provide a new electromagnetic valve, control the same with a timer, and introduce compressed gas in the cylinder into the chamber.

While the embodiment has used a diaphragm pump for enabling switching of decompression•exhaust, a pump of only suction or only exhaust may be employed.

INDUSTRIAL AVAILABILITY

As described above, the capillary cassette according to the present invention is suitable for use as a migration part of a multi-capillary electrophoretic apparatus used for separating/analyzing nucleic acid, protein, peptide, sugar or the like, and particularly suitable for employment for analysis of the base sequence of DNA.

We claim:

1. A gel charging apparatus for charging a gel serving as a medium in which a sample is electrophoresed into a plurality of capillary columns mounted on a multi-capillary electrophoretic apparatus, wherein
end portions on sample injection sides of these capillary columns pass through a holding member of a holder and are two-dimensionally arranged and fixed while keeping airtightness between the same and the holding member to form a capillary cassette, and
the gel charging apparatus comprises a chamber provided with an opening on an upper surface so that closure means inserting end portions on the sample injection sides of said capillary columns inside for closing the opening with said holder is provided in the opening, and is further provided with:

an exhaust port and a release port to the atmosphere;

a gel vessel storing a gel solution so that end portions of said capillary columns on opposite sides to the sample injection sides are dipped therein;

exhaust means provided on the exhaust port of said chamber; and a switching valve provided on said release port.

2. The gel charging apparatus in accordance with claim 1, wherein a flow control valve controlling the flow rate is provided between said release port and said switching valve.

3. A gel charging apparatus for charging a gel becoming a medium in which a sample is electrophoresed in a plurality of capillary columns mounted on a multi-capillary electrophoretic apparatus, wherein end portions on sample injection sides of the capillary columns pass through a holding member of a holder and are two-dimensionally arranged and fixed while maintaining airtightness between the capillary columns and the holding member to form a capillary cassette, and the gel charging apparatus is characterized in comprising a chamber provided with an opening on an upper surface so that closure means inserting end portions on the sample injection sides of said capillary columns in its inner side for closing the opening with said holder is provided in the opening, stores therein a gel solution on positions where the end portions on the sample injection sides of said capillary columns are dipped in the state where said opening is closed with said holder, and is further provided with:

a pressurization port and a release port to the atmosphere;

pressurization means provided on the pressurization port of said chamber, and a switching valve provided on said release port.

4. The gel charging apparatus in accordance with claim 3, wherein a flow control valve controlling the flow rate is provided between said release port and said switching valve.

* * * * *